(12) United States Patent
Dietz et al.

(10) Patent No.: US 6,442,319 B1
(45) Date of Patent: Aug. 27, 2002

(54) CHALCOPYRITE BASED NONLINEAR WAVEGUIDED HETEROSTRUCTURE DEVICES AND OPERATING METHODS

(75) Inventors: Nikolaus Dietz; Klaus J. Bachmann, both of Raleigh, NC (US)

(73) Assignee: Xoetronics LLC, Ringoes, NJ (US)

( * ) Notice: Subject to any disclaimer, the term of this patent is extended or adjusted under 35 U.S.C. 154(b) by 0 days.

(21) Appl. No.: 09/501,401

(22) Filed: Feb. 9, 2000

(Under 37 CFR 1.47)

Related U.S. Application Data (60) Provisional application No. 60/119,295, filed on Feb. 9, 1999.

(51) Int. Cl.[7] .................................................. G02B 6/00
(52) U.S. Cl. ..................................................... 385/122
(58) Field of Search ................................. 385/122–129, 385/147, 12–15

(56) References Cited

U.S. PATENT DOCUMENTS

| | | | | | |
|---|---|---|---|---|---|
| 4,960,319 | A | * | 10/1990 | Dankowych | 385/122 |
| 5,776,375 | A | * | 7/1998 | Hofstraat et al. | 252/582 |
| 5,864,641 | A | * | 1/1999 | Murphy et al. | 385/12 |
| 5,922,537 | A | * | 7/1999 | Ewart et al. | 435/6 |
| 6,122,305 | A | * | 9/2000 | Putnam et al. | 372/94 |

* cited by examiner

Primary Examiner—Akm E. Ullah
(74) Attorney, Agent, or Firm—David P. Krivoshik; Mathews, Collins, Shepherd & McKay (57) ABSTRACT

An optical quantitative detection device comprising: a nonlinear waveguide sensor having a top cladding layer with a top surface for interacting with a target molecule; a second waveguide; a second cladding layer optically coupling the nonlinear waveguide sensor to the second waveguide. Wherein optical excitation of the sensor and optical excitation of the second waveguide enables quantitative discrimination of a target molecule.

20 Claims, 8 Drawing Sheets

CHALCOPYRITE BASED NONLINEAR WAVEGUIDED HETEROSTRUCTURE DEVICES AND OPERATING METHODS

CROSS REFERENCES TO RELATED APPLICATIONS

This application claims the benefit of U.S. Provisional Application Ser. No. 60/119,295 filed on Feb. 9, 1999.

FIELD OF THE INVENTION

This invention relates generally to the optical quantitative determination of active substances, and more particularly to using nonlinear waveguides for quantitative determination.

BACKGROUND OF THE INVENTION

Monitoring the levels of various chemical compounds and agents is important for environmental monitoring, the diagnosis, treatment and control of diseases as well as in law enforcement. Applications for monitoring include compact sensors, applicable to remote, real-time sensing of trace impurities (e.g. greenhouse gases, smog, smoke stack emissions, toxic chemical agents and water pollution to name a few) as well as to medical applications for the recognition of immobilized bio-molecules by means of frequency-agile lasers, and for infrared countermeasures used in the defense industry.

SUMMARY OF THE INVENTION

In accordance with the present invention, there is provided an optical quantitative detection device comprising: a nonlinear waveguide sensor having a top cladding layer with a top surface for interacting with a target molecule; a second waveguide; a second cladding layer optically coupling the nonlinear waveguide sensor to the second waveguide. Wherein optical excitation of the sensor and optical excitation of the second waveguide enables quantitative discrimination of a target molecule.

BRIEF DESCRIPTION OF THE DRAWINGS

A more complete understanding of the present invention may be obtained from consideration of the following description in conjunction with the drawings in which.

DETAILED DESCRIPTION OF VARIOUS ILLUSTRATIVE EMBODIMENTS

The present invention nonlinear chalcopyrite-based waveguide is a non-destructive monitoring device, capable of probing and unambiguously identifying quantitatively a target molecule within a mixed specimen. Because the operational capabilities incorporate several physically distinct modes of operation the nonlinear chalcopyrite-based waveguide has a myriad of potential applications.

Although the present invention nonlinear chalcopyrite-based waveguide is particularly well suited for remote, real-time sensing of trace impurities (e.g. greenhouse gases, smog, smoke stack emissions, toxic chemical agents, water pollution, and other environmental components) it is equally well suited for use in medical applications for the recognition of immobilized bio-molecules by means of frequency-agile lasers, and for infrared countermeasures used in the defense industry.

The development of highly sensitive miniaturized sensor devices, sensing hazard chemicals, viruses/diseases or the failure and potential danger of products, will have a great impact in various areas of our daily life. Easier monitoring of air pollution with quick remote screening and recognition of chemical hazards in the environment enables a faster response to and protection from dangerous situations. Multi-area sensor areas accelerate the detection of biochemical and molecular responses of cells to candidate drugs and speed up the development and compatibility tests of new drugs. For the improvement of the life expectancy of a variety of products, it is quite important to design proper protection layers/coatings that are able to withstand exposure to radiation and/or corrosive environments. The monitoring of the aging process of such protective coatings as well as the warning in the case of a failure is important for at least two reasons: first, for the development of improved coatings and secondly to recognize and counteract failure early on before the product itself is damaged or a hazardous situation occurs.

Figure 1:
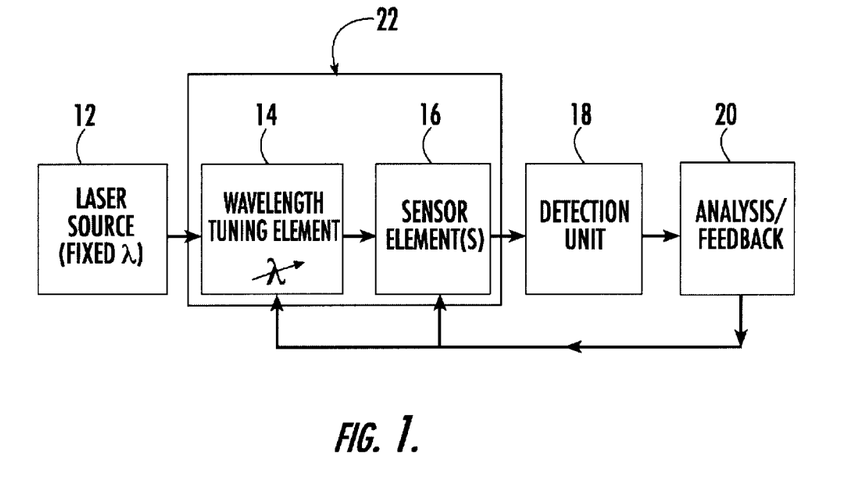
FIG. 1 is a functional block diagram of an integrated sensor arrangement.

Nonlinear interaction of laser light—for example, second harmonic generation (SHG), the sum or difference of frequency mixing, and optical parametric oscillation/optical parametric amplification (OPO/OPA)—can be implemented in waveguided II-IV-$V_2$ chalcopyrite heterostructure layers. Applications for this technology include compact sensors, applicable to remote, real-time sensing of trace impurities (e.g. greenhouse gases, smog, smoke stack emissions, toxic chemical agents, water pollution and other environmental components) as well as to medical applications for the recognition of immobilized bio-molecules by means of frequency-agile lasers, and for infrared countermeasures used in the defense industry. As a result of wavelength tunability the present invention nonlinear chalcopyrite-based waveguide enables discrimination and identification of molecular structures attached to the probe interface. Referring to FIG. 1 there is shown a schematic representation of a sensor based on integrated nonlinear/linear waveguides. The device comprises a laser light source 12, a nonlinear waveguided heterostructure for wavelength/frequency tuning 14, sensing element 16, detection unit 18, and an analysis/feedback unit 20. The laser light source 12 is optically coupled to the nonlinear waveguided heterostructure for wavelength/frequency tuning 14, which is optically coupled to the sensing element 16. The detection unit 18 is optically coupled to the sensing element 16 and coupled to the analysis/feedback unit 20. The analysis/feedback unit 20 is coupled to the nonlinear waveguided heterostructure for wavelength/frequency tuning 14 and to the sensing element 16. A tuner/sensor 22 is comprised of the nonlinear waveguided heterostructure for wavelength/frequency tuning 14 and sensing element 16.

Understanding of the physical principles underlying the operation of such waveguides is essential for the construction of a realistic model to guide their growth, fabrication, and subsequent device testing on single device and integrated system levels. Moreover, an accurate model is a useful complement of the signal processing methodology using conditional probabilities to identify the presence and concentration of a particular molecular species of interest.

Propagation of Light in a Waveguide

Figure 2:
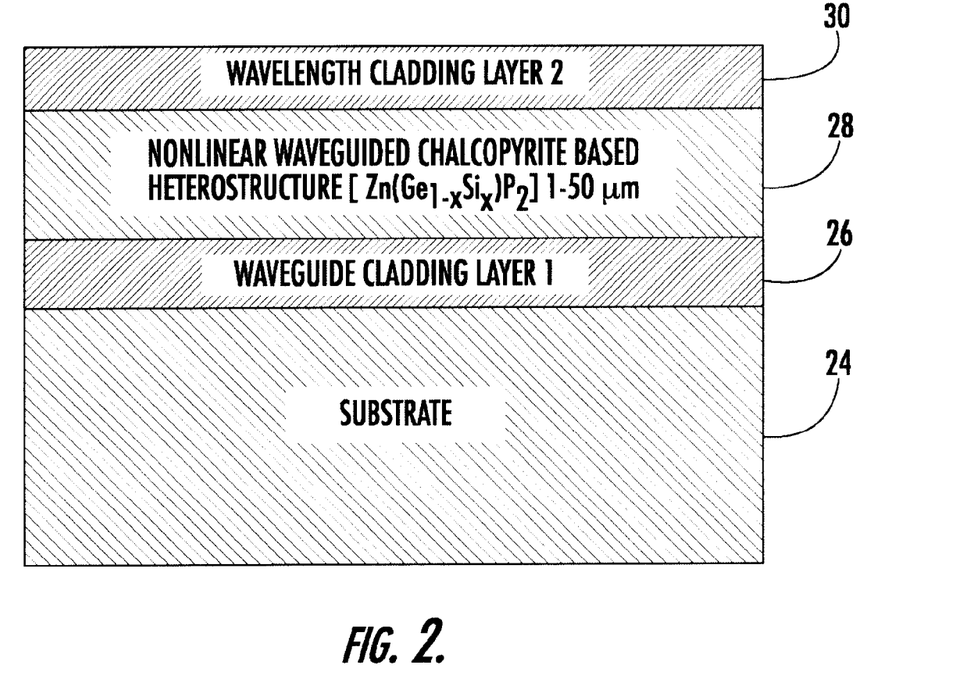
FIG. 2 is a schematic representation of a layered multi heterostructure for a nonlinear waveguide embedded between two lower indexed cladding layers.

Referring to FIG. 2 there is shown, the basic element of the device, a nonlinear waveguiding layer surrounded by waveguide cladding layers. A substrate 24 is covered by a first waveguide cladding layer 26. A nonlinear waveguided chalcopyrite based hetrostructure [$Zn(Ge_{1-x}Si_x)P_2$] 28 of 1 $\mu$m to 50 $\mu$m is on top of the first waveguide cladding layer 26. A second waveguide cladding layer 30 is on top of the nonlinear waveguided chalcopyrite based hetrostructure 28. The propagation of light within devices incorporating linear and/or nonlinear waveguides is described by the Maxwell equations of classical electrodynamics together with the relevant boundary conditions. The four Maxwell equations—the Faraday's law, the Ampere's law, and two Gauss's laws—are solved given the material parameters of the device in question: the widths of the waveguides and the dimensions and the complex indices of refraction in every region of the device. For anisotropic materials, the electric displacement flux density D is related to the electric field E via a tensor relation involving the permittivity tensor $\epsilon$, and the magnetic field H is related to the magnetic field density B via the permeability tensor $\mu$. In the absence of surface currents or surface charge densities, the boundary conditions at the interface of two adjoining regions with different dielectric properties require the continuity of the tangential components of the electric and magnetic fields and of the normal components of the electric displacement and magnetic fields.

The permittivity function E is complex as is the refractive index. Chalcopyrites are uniaxial media with two of the three elements of the permittivity tensor equal to one another and the third, along the optic axis of the medium, is unequal to the other two:

$$D = \epsilon : E,$$

where $$\epsilon = \begin{bmatrix} \epsilon & 0 & 0 \\ 0 & \epsilon & 0 \\ 0 & 0 & \epsilon_z \end{bmatrix}$$

while $$B = \mu : H.$$

The c-axis (optical axis) of chalcopyrites is taken to be the z-axis. For the positive uniaxial medium, $\epsilon_z > \epsilon$, and for the negative uniaxial medium, $\epsilon_z < \epsilon$.

The chalcopyrite layer 28 is characterized by an ordinary and an extraordinary indices of refraction, $n_o$ and $n_E$, respectively. The c-axis of chalcopyrite can be oriented at an arbitrary angle with respect to the growth axis of the layer structure. Different c-axis orientations can be obtained by the use of different substrates and different substrate orientations.

The electromagnetic wave (harmonic field) solutions of the Maxwell equations in homogeneous media (those with spatially uniform dielectric properties) are plane waves of the form $\exp(ik \cdot r - \omega t)$, where k is the propagation constant is and $\omega$ is the light frequency. In an isotropic medium characterized by a single dielectric constant, the propagation constant perpendicular to both E and H, and is given by $k = \omega \sqrt{\mu \epsilon}$. In a uniaxial (or birefringent) medium, two types of waves can be propagated:

1) Ordinary wave, which is polarized in the y direction, with the propagation constant $$k = \omega \sqrt{\mu \epsilon}$$

2) Extraordinary wave, which is polarized in the xz-plane, with the propagation constant perpendicular to the displacement and magnetic fields. The phase velocity of the extraordinary waves depends on the angle of propagation with respect to the optic axis.

For propagation along the optic axis, the two waves are degenerate.

The principles outlined above find their application in the design of optical waveguides in isotropic and uniaxial media. The waveguiding layers of one representative embodiment of the present invention are in the form of dielectric slabs, although the operational principles contained herein equally apply to rectangular and other cross section dielectric guides as well. Consider a symmetric slab waveguide whose thickness is d in direction x and the yz-plane is the plane of the waveguiding layer. The field solutions are either transverse electric (TE) or transverse magnetic (TM) modes. In TE polarization, the guided mode is in the z-direction and the electric field is in the y-direction. The electric field profile in the x-direction is a standing wave in the waveguiding region and a decaying exponential in the surrounding cladding regions. Both even and odd modes can be propagated provided a guidance condition (based on the solution of the wave equation and boundary conditions) is satisfied. Solutions are found up to a cutoff frequency, which can be varied with the choice of the waveguide thickness and the refractive indices of the guide and the cladding regions. This demonstrates one of the important features of the present invention's frequency or wavelength selectivity. At the same time, the decay constant of the fields penetrating into the adjoining cladding layers, or equivalently the optical confinement factor of the guided mode can be controlled. For semiconductor materials, the permittivity function is frequency dependent. Similarly, for the TM modes, the magnetic field is polarized in the y-direction while the wave is guided in the z-direction. The TM modes have their own analogous guiding conditions and confinement factors.

In asymmetric dielectric slab waveguides, the dielectric properties of the two cladding regions 26 and 30 on either side of the waveguide 28 are different. Therefore, the solutions do not have pure even or odd parities, and the field distributions in the x-direction are nonsymmetric. However, this asymmetry is yet another degree of freedom in devising mode profiles, in particular the decay profiles in the cladding regions. The corresponding guiding and cutoff conditions are suitably modified, which is described in S. L. Chuang, *Physics of Optoelectronic Devices*, Wiley, N.Y., 1995 and which is incorporated herein by reference. In real devices, the possibility of losses (or even gains), thus complex permittivities, must be accounted for in the design of the waveguides.

Nonlinear Optics

In linear optical materials (media), the induced polarization is proportional to the electric field that induced it; in nonlinear optical (NLO) materials (media), the polarization response is proportional to the square of the electric field.

The nonlinear physical properties of chalcopyrites derive from their tetragonal symmetry. Because the growth direction is fixed for a given substrate orientation, a phase matching can be achieved by the lateral confinement and guiding of the incoming light beam. Therefore, one task of the modeling effort is to predict the conditions necessary to achieve the desired tunability. For ease of tunability, the model varies the launch angle in the nonlinear waveguide (which will change the angle of phase matching) and the change of the refractive indices of the nonlinear waveguide and the cladding layer with an integrated electrical field modulator.

One of the effects of nonlinearity is the exchange of energy between electromagnetic fields of different frequencies, among them SHG, sum or frequency mixing, and OPO/OPA. For example, the nonlinear waveguided heterostructures can be used for: generation of coherent infrared laser light by second-harmonic generation (SHG); and, generation of coherent infrared laser light by frequency difference/sum mixing generated light by interaction with probe beam in below/above waveguides.

The formalism governing the propagation of waves in nonlinear media begins with the Maxwell equations. In the NLO media, the total polarization is separated into its linear and nonlinear portions. In SHG, an input field (the pump beam) at frequency $\omega$ generates a field at frequency $2\omega$. Efficient generation of the second harmonic field (i.e., the conversion efficiency) requires that the propagation vectors of the pump beam and of the SH beam be equal—the so-called phase-matching condition. Equivalently, refractive indices of the waveguided layer for the pump beam (fundamental) and the SH beam frequencies must be equal.

The phase matching condition can be satisfied in uniaxial materials when the fundamental and the SH beams are of different types—one an ordinary and the other, an extraordinary beam. Since the index of refraction of the extraordinary beam is a function of the angle between the propagation direction and the crystal optic axis, it is possible to find the angle of launch for which the ordinary index of refraction of the fundamental wave is equal to the index of refraction in the waveguided layer for the extraordinary beam at twice the fundamental frequency. An additional consideration is the depletion of the pump beam for large conversion efficiencies, which is possible with material with large NLO coefficients and long interaction paths. Special confinement schemes can also boost the conversion efficiencies.

Another useful NLO effect is optical parametric amplification (OPA) which involves the transfer of power from the pump beam at frequency $\omega_3$ to waves at frequencies $\omega_1$ (signal) and $\omega_2$ (idler), with $\omega_3=\omega_1+\omega_2$. In OPA, the input consists of the pump beam and the idler beam, and the output is the signal beam frequency. As in SHG, the conversion efficiency—here, called the gain coefficient—requires that a phase matching condition is satisfied, wherein the sum of the propagation coefficients of the signal beam and idler beam is equal to that for the pump beam. That is, $k_3=k_1+k_2$. A related effect is OPO—the optical parametric oscillation—in which a nonlinear crystal is placed within an optical resonator that provides resonances for the signal and/or idler waves. At some threshold pumping intensity, the parametric gain causes a simultaneous oscillation at the signal beam and idler beam frequencies. At the threshold, the power loss from the pump beam and idler beam is just offset by the power gain of the signal beam. The merit of such power conversion is that the idler and signal frequencies can be tuned continuously over large frequency ranges by changing the angle of launch with respect to the crystallographic axes.

This property is further described in A. Yariv, *Optical Electronics*, 4$^{th}$ ed., Holt, Rinehart and Winston, Philadelphia (1991) which is incorporated herein by reference.

Phase matching for specific applications like second harmonic generation (SHG) and optical parametric oscillation (OPO) in birefringent nonlinear semiconductor waveguides have the flexibility of achieving phase matched coupling between different modes of the guide, a decided advantage over phase matching in bulk materials. This allows phase matching over a much wider wavelength range than is possible in the bulk.

Figure 3A:
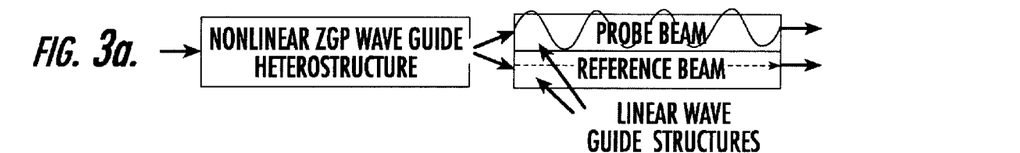
FIGS. 3a, 3b, and 3c are a detail of the wavelength selection and sensor probe areas.
Figure 3B:
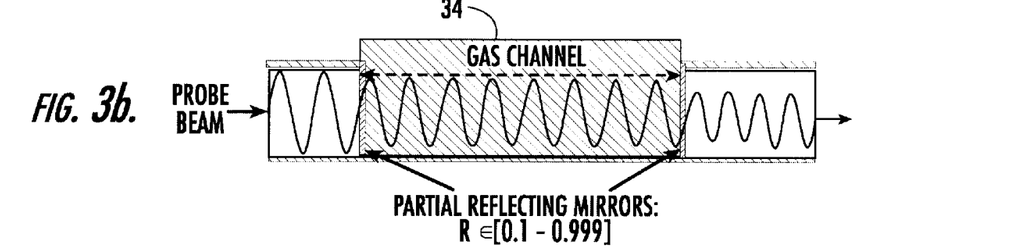
Figure 3C:
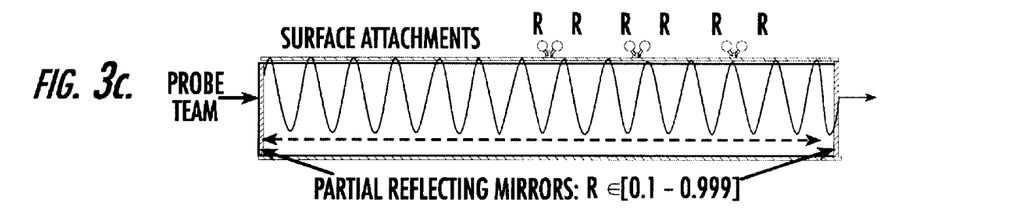

Referring to FIGS. 3a, 3b and 3c there are shown graphic representations of the application of NLO effects in a nonlinear chalcopyrite-based waveguide structure for generating/mixing laser light. Such an application is useful in generating laser light in a wavelength region near a specific resonance frequency of an adsorbed molecule at a surface or a specially prepared interface. With proper waveguide design, this structure will have a precise control of phase matching and frequency interaction and a selection of propagation modes.

Electro-Optical Effect

The propagation of light can be modulated with applied electric fields. The application of the electric field in an electro-optic medium changes its so-called index ellipsoid by the amount proportional to the product of the applied electric field and the material's electro-optic tensor. This tensor is zero for centrosymmetric materials, but is nonzero in chalcopyrites. As a result, the index ellipsoid rotates in space, which means that the polarization directions and the indices of refraction of the ordinary and extraordinary waves rotate with it. This electric-field induced birefrigence can be used to produce a phase retardation of one polarization component with respect to another—thus the state of polarization—which can be used for amplitude modulation (with the use of polarizers). Since the index of refraction is field dependent, another application of the eletro-optic effect is the control of the phase of a wave, including phase modulation, by the applied field.

With electric field tuning of the refractive indices (via the electro-optic effect, also called the Pockels/Kerr effect—linear/nonlinear components), the coupled waveguides can be used as optical filters for selecting the frequencies that can propagate in the device or as optical waveguide switches for transfer of power from one waveguide to another. In waveguides, the confinement of the optical radiation to dimensions comparable to the wavelength makes it possible to achieve the magnitude of electric fields that is necessary for modulation with relatively small applied biases. Also, the absence of diffraction in a guided optical beam makes it possible to use longer modulation paths. Referring again to FIGS. 3a, 3b and 3c there is shown the device configuration in which the electro-optic effect can be used for amplitude and phase modulation. Such modulation allows for phase sensitive detection, thus a cleaner signal extraction from the inevitable background noise and for its subsequent use in the signal analysis of the output data.

A special subset of nonlinear optics deals with the interaction of light and sound—the acousto-optic effect. It is related to the change of the optical properties of a medium upon the passage of a sound wave, which changes the density of the material and its state of strain, thereby its local refractive properties.

Coupled Waveguides

Figure 4:
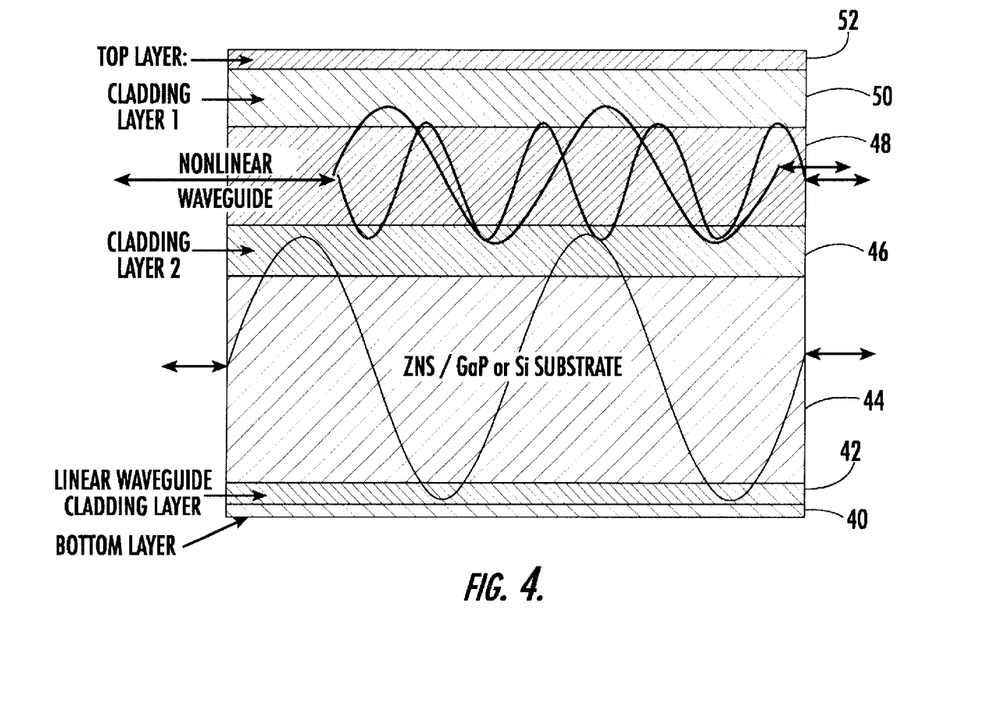
FIG. 4 is a schematic representation of a layered double waveguide heterostructure, where the substrate itself is used as a linear waveguide.

Referring to FIG. 4 there is shown one embodiment of a double waveguided device structure, here a linear— substrate-based waveguide and a nonlinear $ZnGeP_2$ waveguide layer. A bottom layer 40 is covered by a linear waveguide cladding layer 42. A substrate-based waveguide 44 such as ZnS/GaP or Si covers the linear waveguide cladding layer 42 and is covered by a second cladding layer 46. A nonlinear $ZnGeP_2$ waveguide layer 48 is on top of the second cladding layer 46. A first cladding layer 50 is on top of the nonlinear $ZnGeP_2$ waveguide layer 48 and has a top layer 52 on top of it. With proper design of the cladding structure(s) 46 between the two waveguides 44 and 48 (denoted as coupling area), waves propagating in these two waveguides 44 and 48 can interact in the coupling region of the second cladding structure 46. As a result, the NLO frequency generation in the NLO layer can be altered if the wave in the linear layer 44 modulates the optical and electrical properties in the birefringent nonlinear waveguided layer 48.

Consider the coupling of two waveguides, for example, the nonlinear/linear waveguide combination (shown in FIG. 4) or a nonlinear/nonlinear waveguide combination. The coupling is analogous to that of two LC circuits or of two coupled pendulums. Consider two waveguides 44 and 48 shown in FIG. 4. When isolated, each waveguide has a separate modal distribution in the xy-plane, which is perpendicular to the waveguiding direction z. Waveguides 44 and 48 support one or more guided modes each. The total electric field solution is a linear superposition of the individual waveguide modes with z-dependent amplitude coefficients as is the total magnetic field solution. These amplitudes satisfy a set of coupled linear differential equations which express the coupling between waveguides 44 and 48, which can be cast in the form of an eigenvalue-eigenfunction problem for the eigenstate solutions of the coupled system of two waveguides. There are two eigenvalue and associated eigenvector solutions for both codirectional and contradirectional couplings. In general, the eigenmode solutions arc either in phase or out of phase. The power transfer from one waveguide to another can be either synchronous or asynchronous depending on whether waveguides 44 and 48 are similar or not.

Coupled mode theory for anisotropic waveguides is known to those skilled in the art. Further information can be found in the following publications, which are incorporated herein by reference: D. Marcuse, Bell Syst. Tech. J. 54, 985–995 (1975); A. Hardy, W. Streiffer, and M. Osinski, Opt. Lett. 11, 742 (1986); and L. Tsand and Sl. Chuang, J. Lightwave Technol. and IEEE J. Quantum Electron. 6, 832 (1988).

Figure 5:
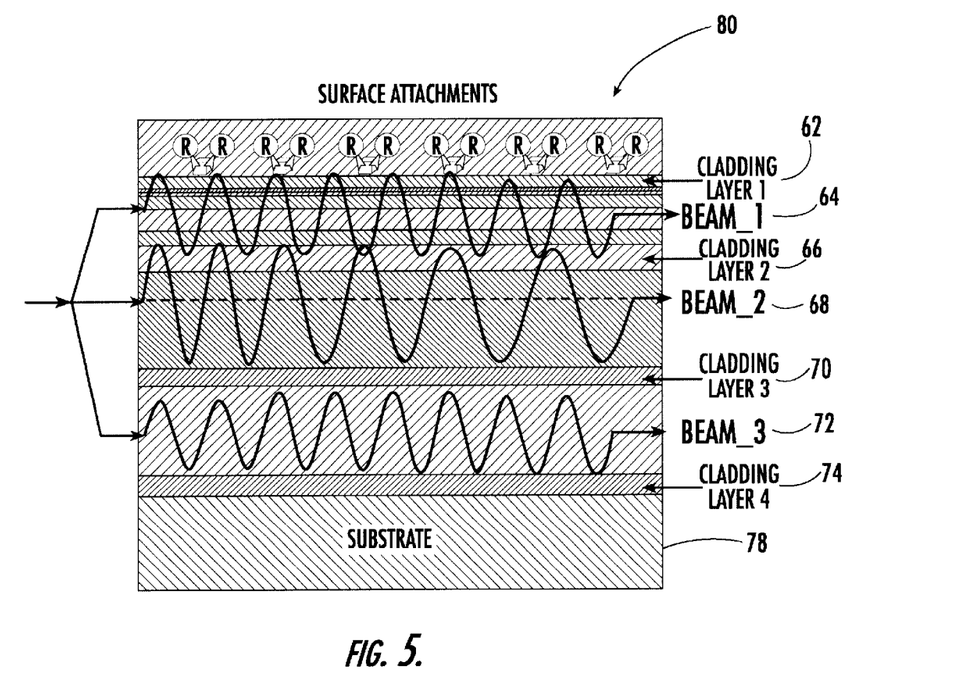
FIG. 5 is a schematic representation of a multiple layered linear/nonlinear waveguided heterostructure.

Because waveguide directional couplers can perform power division, modulation, switching, frequency selection, and polarization selection, a number of unique devices can be constructed with a double waveguide structure. For example, a modification/altering at the $ZnS_{1-x}Se_x$/ $SiO_2$/ $Si_3N_4$ interface surface (see for instance first cladding layer 62 shown in FIGS. 5 and 6) will change not only the phase condition and amplitude of Beam 1, but will also change the wave interaction/propagation (Beam2) in the nonlinear waveguide layer 68. Setting the proper phase matching conditions, the phase shift and amplitude changes of Beam 1 can be translated into a frequency shift of the light generated in the nonlinear waveguide(s) 68. This enables the building of highly phase-sensitive surface detectors, where surface induced phase changes are analyzed by a frequency shift in Beam 2. Referring to FIG. 5 there is shown an illustration of a sensor device structure 80 built up from multiple waveguide structures. Beam 1 is the probe beam, which interacts with the surface/interface to sense surface attachments/modifications. Beam 3 is a reference beam embedded in the cladding layers 3 and 4, with a defined phase and amplitude correlation to Beam 1. Beam 1 and Beam 2 are coupled via the second cladding layer 66, which allows interactions between both beams 1 and 2 as well as a modification of the properties in the third cladding layer 70 and the underlying nonlinear waveguide layer by Beam 1. Phase and/or amplitude changes in Beam 1 upon surface attachments/modifications 60 can be analyzed by Beam 2 and by comparing Beam 1 with Beam 3. The detection process can involve an interference process of the beams with each other, a nonlinear light difference generation process, and/or a light upconversion process.

Figure 6:
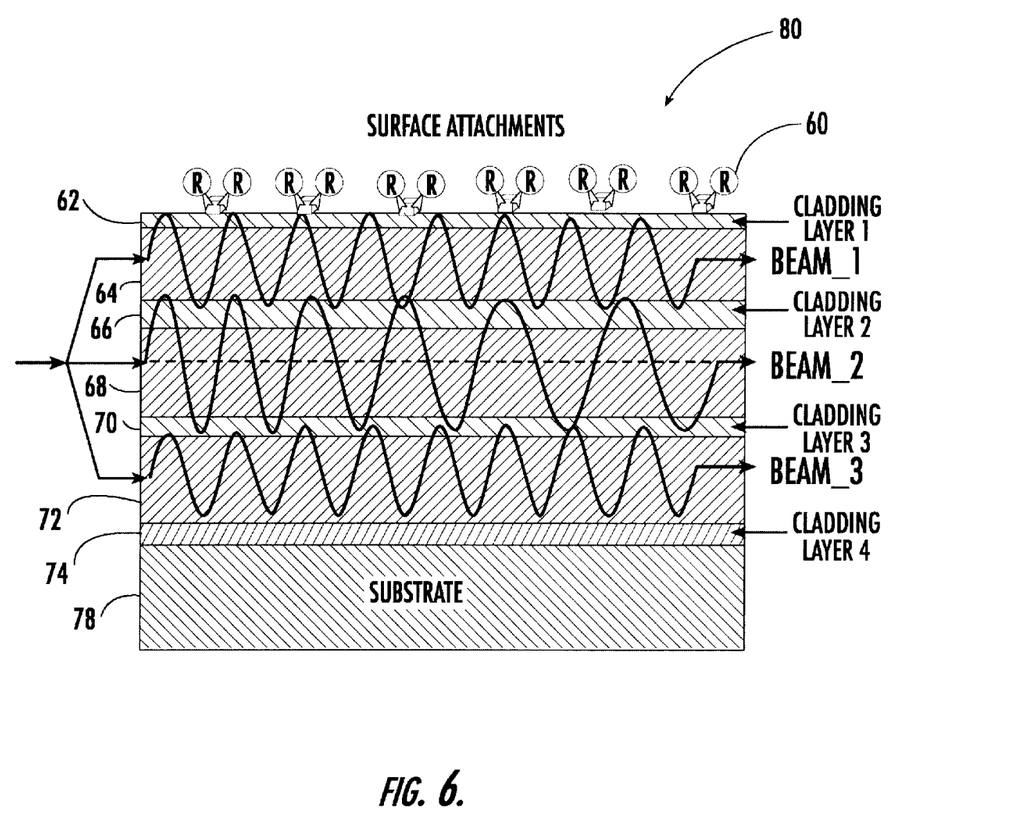
FIG. 6 is a schematic of a differential sensor configuration using multiple layered linear/nonlinear waveguided heterostructures to characterize surface attachments.

Referring to FIG. 6 there is illustrated a differential sensing technique, where Beam 1 (probe beam) and Beam 3 (reference beam) symmetrically interact with Beam 2. Assuming an interference based detection between Beam 1/Beam 2, Beam 2/Beam 3, and Beam 1/Beam 3, differential signal(s) can be generated by (a) interference of the beams, (b) phase shifted interference [nulling configuration], (c) difference and sum frequency mixing, or (d) second harmonic generation. The resulting output can than be directly related to surface/interface modifications at the first cladding layer 62.

The above mentioned waveguide configurations shown in FIGS. 5 and 6 are not limited to surface attachments. As illustrated in FIG. 3b, the inset of a channel 34 where the probe beam interacts with a gas volume will lead similarly to a phase shift and/or amplitude change, which can be analyzed as described above. The above-described configurations are not limited to coupled linear/nonlinear waveguides. The description can be also applied to two or more nonlinear waveguides that are coupled to each other. If a nonlinear waveguide is used to probe surface attachments, it is difficult to separate the effects related to a surface/interface modification due to an attachment of molecules at the surface from the effects related to the interaction between two nonlinear waveguides. However, by using a differential beam configuration as shown in FIG. 6, the coupling effects between second cladding layer 66 and third cladding layer 70 are for the probe beam (Beam 1) and the reference beam (Beam 3) identical, and a differential signal—related to surface processes-can be extracted.

Light/Sensor Area Interaction

The probe/sensor module shown in FIGS. 3, 4, 5 and 6 is modeled as an area where selected beam(s) interacts with a medium or surface/interface interface with the intent to analyze any modification of such an. interface/surface. A suitable detection area to monitor/characterize and identify surface attachments, may require an additional sensitized surface reaction layer. The reaction layer is thin on the scale of optical wavelengths and its optical dielectric properties are altered upon reaction(s) with a specific molecule, antigen or antibody. For model development, the sensor area with attached absorbent on the surface can be modeled in a number of ways. The simplest approach is to use an effective medium approach wherein a thin virtual interlayer is interposed between the ambient and the probing waveguide. This layer is characterized by its own indices of refraction, reflecting the absorptive processes occurring on the surface. As these are proportional to the concentration of chemical/biological agents attached to the surface, the wave/sensor area interaction varies in direct proportion to the concentration of CB agents being probed.

A probe beam, such as Beam 1 in FIG. 5, interacting with the surface suffers an amplitude and a phase change proportional to the concentration of the CB agents being probed. The probe beam interacts with Beam 2 of the NLO guide in the intervening interaction region. Since the light frequency in the NLO guide depends on the phase matching condition and the refractive indices of the cladding layers, the presence of CB agents results in the frequency shift of Beam 2.

Baseline Nonlinear Waveguide Structure/Principle

Nonlinear interaction of laser light as for example observed in second harmonic generation (SHG), sum or difference frequency mixing, optical parameter oscillator/amplifier (OPO/OPA) are achieved in waveguided II-IV-V$_2$ chalcopyrite heterostructure layers.

One particular focus is in near lattice matched nonlinear $Zn(Ge_{1-x}Si_x)P_2$ chalcopyrite compound heterostructures on II-VI, III-V and Si semiconductor compound substrates. The nonlinear layer is embedded between two layers/interfaces with lower refractive indices, forming the cladding layers. Cladding layers include for example $Ga_{1-x}Al_xP$, $ZnS_{1-x}Se_x$, $CaF_2$, or graded $Zn(Ge_{1-x}Si_x)P_2$ layers on GaP, ZnS or Silicon substrates. The active wavelength range for $Zn(Ge_{1-x}Si_x)P_2$ extends from 0.6 μm to 13 μm.

The use of a nonlinear waveguided heterostructures can provide the added flexibility of being able to adjust the effective guide index by varying the thickness and cladding geometry to achieve appropriate phase matching conditions for a wide variety of both sensor and infrared countermeasures applications. This can also be combined with variation in the angle between the propagation vectors of the pump and probe radiation fields and the principal optic axis of the tetragonal $ZnGeP_2$, as would be possible when this axis is grown in the plane of the guide. Thus, additional mixing configurations may be realized that may not be possible in nonlinear bulk material.

The present invention has a variety of embodiments including:

a. Any heterostructure combination that uses single or multiple birefringentchalcopyrite layers as nonlinear waveguided material.
b. Any combination of cladding material, that is lattice-matched to $Zn(Ge_{1-x}Si_x)P_2$ such as $Ga_{1-x}Al_xP$, $ZnS_{1-x}Se_x$, $CaF_2$, graded $Zn(Ge_{1-x}Si_x)P_2$, $Ge_{1-x}Si_x$, Si or a combination of it.
c. Si, GaP, $Ga_{1-x}Al_xP$, $ZnS_{1-x}Se_x$, or $Ge_{1-x}Si_x$ substrate material for nonlinear $Zn(Ge_{1-x}Si_x)P_2$ wave guides.
d. Any planar (and horizontal structured) heterostructure using $Zn(Ge_{1-x}Si_x)P_2$ as active nonlinear waveguide and materials combination in (a)–(c) as substrate/cladding layer or a combination of it.
e. Any structure that uses the principal structure described in (a)–(d) in a multiple nonlinear waveguide layer stack, where the nonlinear active area is based oil a chalcopyrite layer.
f. Any nonlinear optical or electro-optical device principle based on (a)–(d), deposited epitaxially, polycrystalline or microcrystalline, or containing $Zn(Ge_{1-x}Si_x)P_2$ material.
g. Any nonlinear optical or electro-optical device whose principle is based on (a)–(d) and contains lateral confinements (horizontal structuring of cladding layer and/or nonlinear waveguide) that can adjust phase matching conditions.
h. Any device application/combination that uses the principal structure described in (a)–(d) for optical mode selection or filtering.
i. Any device application/combination that uses the principle structure described in (a)–(d) for frequency selection, tuning or frequency shift.
j. Any kind of modulation of the physical properties of cladding layer and/or nonlinear waveguide layers—described in (a)–(d)—, aiming to change/alter optical phase matching conditions and/or electro-optical properties. Examples: (a) electrical, magnetic, microwave-, acoustic field modulation, (b) internal modulated electron field or optical properties generated by acoustic -, microwave-, or any electromagnetic radiation.

TABLE 1

Materials Selection

| Sub-No. strate | 1st Cladding layer: Substrate <-> waveguide | Waveguide | 2nd Cladding layer: waveguide <-> top |
|---|---|---|---|
| 1 GaP | $Ga_{1-x}Al_xP$ (x = 0 – 0.5) | $ZnGeP_2$ | $Ga_{1-x}Al_xP$ (x = 0 – 0.5) & thick $GaP/Zn(Se_xS_{1-x})$ top layer |
| 2 GaP | $Zn(Ge_{1-x}Si_x)P_2$ (x = ) – 0.05) | $ZnGeP_2$ | $Zn(Ge_{1-x}Si_x)P_2$ & thick $GaP/Zn(Se_xS_{1-x})$ top layer |
| 3 Silicon | $Zn(Ge_{1-x}Si_x)P_2$ (x = decreasing) | $ZnGeP_2$ | $Zn(Ge_{1-x}Si_x)P_2$ & thick $GaP/Zn(Se_xS_{1-x})$ top layer |
| 4 Silicon | GaP followed by $Zn(Ge_{1-x}Si_x)P_2$ (x = decreasing) | $ZnGeP_2$ | Graded Zn $(Ge_{1-x}Si_x)P_2$ layer with increasing x |
| 5 Silicon | GaP followed by $Zn(Ge_{1-x}Si_x)P_2$ (x = 0 – 0.5) | $Zn(Ge_{1-x}Si_x)P_2$ fixed composition | $Ga_{1-x}Al_xP$ (x = 0 – 0.2) & thick $GaP/Zn(Se_xS_{1-x})$ top layer |

Referring to Table 1, there is shown material selection as an example for a composed ear waveguide structure integrated on Silicon, GaP or other lattice matched substrates. Not listed are lattice-matched materials such as $Zn(S_{1-x}Se_x)$, $CaF_2$ and other, lattice-matched materials combinations to the choice of substrate, cladding layer or $Zn(Ge_{1-x}Si_x)P_2$ waveguide layer.

Double/Multiple Waveguide Structure/Principle

Using a wave-guided nonlinear heterostructure such as described in the variety of embodiments above, the substrate material, for example Si, $ZnS_{1-x}Se_x$, or $Ga_{1-x}Al_xP$, or a second heterostructure layer, for example a III-V compound semiconductor layer, can be used as a second waveguide layer (optically linear or nonlinear), which is able to interact with the nonlinear waveguided chalcopyrite heterostructures as illustrated in FIG. 4.

As can be seen in Table 1, a preferred substrate material choice for a nonlinear II-IV-V2 heterostructure may be Si, GaP or $ZnS_{1-x}Se_x$. Silicon is an attractive substrate material for several reasons: readily available large, high quality substrates, up to 10 inch diameter; the refractive index is higher than GaP, $Ga_{1-x}Al_xP$, $ZnS_{1-x}Se_x$, or $Zn(Ge_{1-x}Si_x)P_2$; and, the substrate is transparent from 1.1 μm to 13 μm, allowing the use of probe light (laser light) from near-infrared to mid-infrared, which basically matches the transparency range of the nonlinear $Zn(Ge_{1-x}Si_x)P_2$ layer.

GaP or $ZnS_{1-x}Se_x$ substrates might be preferred, since the transparency region extends further in the visible range up to 0.5 μm. $Ga_{1-x}Al_xP$ (x>0) has a lower refractive index and can therefore act as a cladding layer of GaP as well as for the nonlinear $Zn(Ge_{1-x}Si_x)P_2$ layer. Since the differences in refractive indices are very small, large interaction regions can be achieved. The first cladding layer, (ambient/cladding layer/probe beam wave guide) can be any low refractive index material, for example $ZnS_{1-x}Se_x$, $CaF_2$, $SiO_2$, or $Si_3N_4$—or a combination of it. The deposited material(s) can be epitaxial, amorphous, organic polymers, organic interlayer, water or any material with a lower refractive index than the underlying first wave guide.

Further embodiments of the present invention include:
a. Any multiple heterostructure which includes at least two waveguided structures that can interact and influence each other, and where at least one of them acts as a nonlinear optical waveguide structure.
b. Any heterostructure combination that uses the substrate material as an additional waveguide structure.
c. Any combination of cladding materials that can act as a cladding layer between two waveguided structures to achieve coupling between these both waveguide heterostructures. Any combination of cladding materials deposited on a substrate to make the substrate an additional waveguide structure. The cladding layers do not have to be epitaxial; they can be for example amorphous, made out of polymer, an organic, biological materials, or a combination of it.
d. Any planar (and/or horizontal structured) heterostructure combination using the principle described in (a) and (c).
e. Nonlinear frequency convert ion and probing, resulting from interactions between coupled waveguides.

Phase-Frequency Converter

Using the base principles previously described and defined one preferred base structure is based on the conversion of optical phase and amplitude information into a frequency shift. Phase information and or phase shifts—as they occur by interacting with an interface/surface—may be hard to detect. Interference techniques are typically used to measure such optical phase shifts. The principle of a "phase-frequency converter" (PFC) is based on a double waveguide structure as schematically shown in FIG. 4. It can be built up by an linear optical waveguide that is coupled to a nonlinear waveguide (see FIG. 4), or by two nonlinear waveguide structures that are coupled via a coupling layer, which can be the cladding layer. between the wave guides, as previously described. The beam, which phase and amplitude is subject for analysis, will be denoted in the further text as probe beam. The probe beam, traveling either in the linear waveguide or in the outer nonlinear waveguide, which is characterized by at least: a coupling area to the nonlinear waveguide, which light (radiation) frequency depends on the phase matching condition and refractive indices of the cladding layers; a surface/interface that is subject to be probed and induces a phase and amplitude change in the probe beam; and, a surface/interface which is subject to be probed and where the surface induced changes (wavelength specific absorption or wavelength specific phase changes) are used to modify the conditions of the second waveguide, which then is subject of detection.

Still further embodiments of the present invention include:
a. Any heterostructure waveguide combination that probes a surface/interface and translate the surface/interface modification in a frequency shift using a nonlinear waveguide layer;
b. Any combination that is based on a double or multiple waveguide structure, where the wavelength specific phase changes/information of the beam in one waveguide is translated in a frequency change/information in another nonlinear (chalcopyrite) waveguide—and vice versa;
c. Any combination that is based on a double or multiple waveguide structure, where wavelength specific absorption information in one waveguide is translated into a frequency change/information in a second nonlinear waveguide layer—and vice versa;
d. Any multiple linear/nonlinear or nonlinear/nonlinear waveguided heterostructure combination with differential signal detection as for example illustrated in FIG. 5 and FIG. 6;
e. Any combination of (a) through (d) with added partial reflected side faces as illustrated in FIG. 3c;
f. Any combination of (a) through (d) with gas channel inset(s) (with or without partially reflecting side faces) in the probe beam area as illustrated in FIG. 3b;
g. Any combination of (a) through (fi, which uses a beam-interference technique for signal detection, phase analysis, and/or signal analysis or signal differentiation;
h. Any combination of (a) through (f), which uses an interference approach between probe and reference beam (or interference difference between two frequency shifted beams) for signal detection;
i. Any combination of (a) through (f) with added phase shifter ($\lambda/4$-shifter) in one of the beams used for signal nulling in an interference detection system; and,
j Any combination of (a) through (i) with additional beam mixing, using difference frequency, sum frequency or second harmonic conditions.

The principle of a PFC is not restricted to a chalcopyrite based nonlinear heterostructure. It can be any nonlinear material combination that fulfills the requirements described above. Such a combination can be for example a strained III-V semiconductor multi-heterostructures, which acts as a nonlinear waveguide element. Other examples include nonlinear waveguided organic layers, or waveguided layers made out of BBO, LBO, . . . material.

Compact, Integrated Sensors Based on Nonlinear Waveguided Heterostructures

A fully integrated sensor contains a light source, a nonlinear waveguide heterostructure, described in the first two sets of embodiments, a probe/sensor module, and a detection module. The PFC sensor described in the third set of embodiments is one example for a sensor module in this context. The high level functional diagram of such an integrated sensor arrangement is shown in FIG. 1. The sensor arrangement includes a light source 12, a chalcopyrite based nonlinear waveguided heterostructure 14, a sensor area 16 where selected beam(s) interacts with a surface/interface, a detection area 18, and an analysis/feedback element 20. The components can be either monolithically integrated on one substrate, a hybrid-solution (for example. micro-bonded heterostructures), or can be linked via optical connections (waveguides) to each other in close proximity. Both the chalcopyrite based nonlinear waveguided heterostructure 14 and the sensor area 16 can be merged as demonstrated on the PFC structure.

The light sources for the nonlinear layer heterostructure, described in the various embodiments, can be coupled in using standard techniques such as micro prism. A more advanced structure can use integrated laser light source, either monolithic integrated or micro-bonded laser diodes of various kinds.

Similar as to the integration of the light source, the detector area can be monolithically integrated on the same substrate the nonlinear waveguide structure has been grown/attached. It can be micro-bonded to the substrate or it can be linked to an external structure.

Exemplary Applications

The various embodiments of the present invention described above are the base for various types of sensors detecting chemicals, trace impurities in air or liquids, enzymes, biological agents, or biological hazards. The simplest case is the identification of chemical atoms/molecules in an ambient, for example air or water. The attachment of these chemicals to the probed surface/interface lead to a change of the interfacial properties, which are detected via an induced phase shift and/or the wavelength specific absorption features of the specific chemical. Sensors to detect air pollution ($CO_x$, $No_x$, etc.), monitor trace impurities in the exhaust of power stacks or car engines, or analyzing contamination in water are some examples of applications. Other applications include:

Effects of air pollution/sources of air pollution/time evolution of air pollution Photochemical effects of air pollution Physical Chemistry and Corrosion in the Environment Chemical gas sensors for monitoring air quality in laboratories, offices, and homes.

Catalytic Converters

Monitoring of the Ozone Layer (Halogens and Ozone Depletion)

To analyze and identify more complex biological agencies as for example needed to identify biological hazards in the environment or for medical applications may require the surface/interface to be prepared and/or sensitized for the specific biological agent in mind. The surface/interface may include a sensitized surface reaction layer, which is altered in its optical dielectric properties upon reaction(s) with a specific molecule, antigen or antibody.

Figure 7:
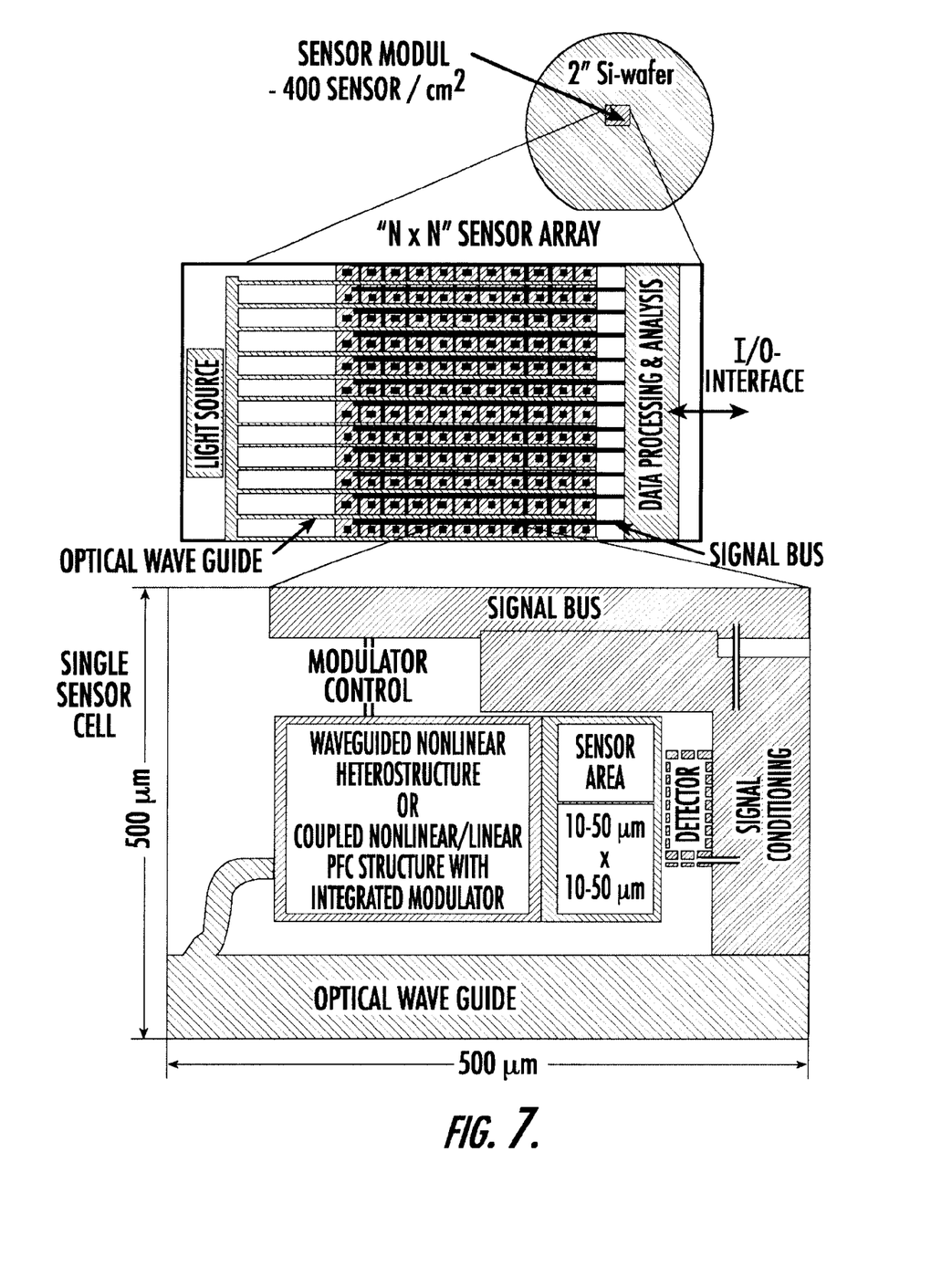
FIGS. 7 shows an integrated multi-area sensor module.
Figure 8A:
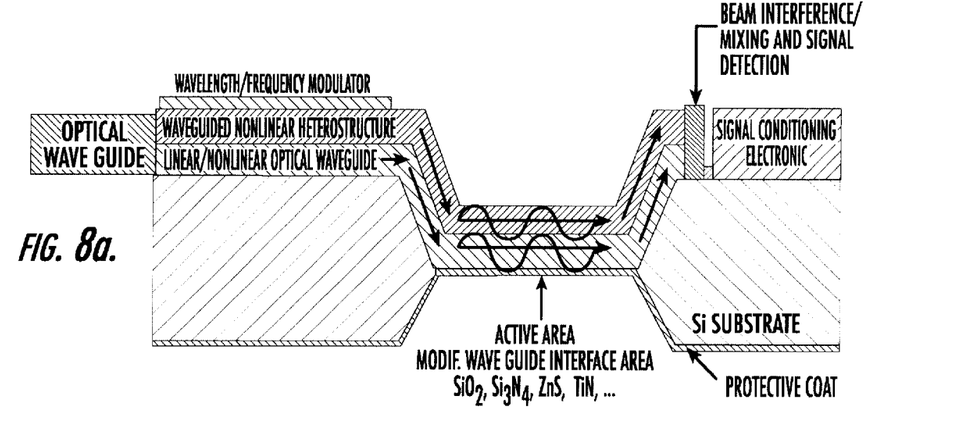
FIGS. 8a and 8B are a cross-sectional view of the integrated multi-area sensor cell.
Figure 8B:
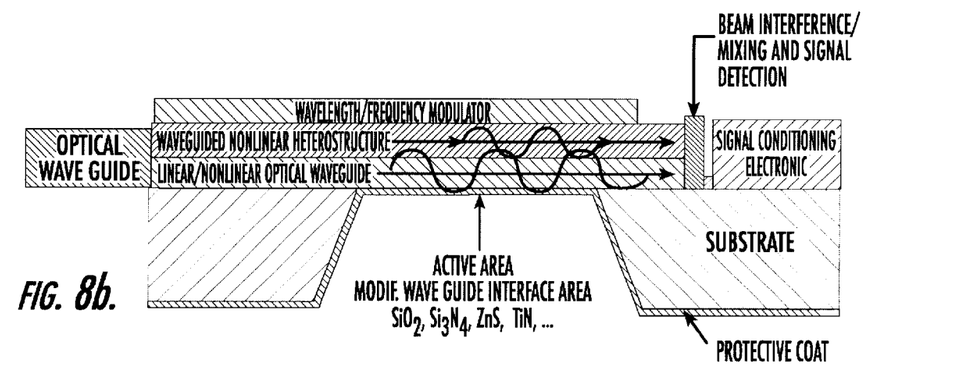

Referring to FIGS. 7 and 8 there is shown schematically a multi-area sensor module, wherein each sensor-cell can be prepared/sensitized for one specific molecular structure, allowing the screening of a sample in investigation to a series of possible reactions. This is of specific interest for many medical applications, such as for allergic tests or screening for common diseases. Enhancement to specific agencies can be achieved by electrical field-modulated of the surface/interface structures for phase sensitive detection and/or to enhance/suppress surface reactions. Examples to achieve enhanced sensitivity are:

electrical or magnetic biasing of active surface/interface for cleaning/reactivating of active surface ionizing of molecules (enhancing of reactions)

trapping of molecules

Specific fields of applications can include:

Sensors to identify and monitor complex biological structures

Medical sensors to identify viruses and diseases

Multi-area sensors for medical screening.

Compact multi-area sensors to monitor chemical and biological hazards in the environment.

A further area of application is the sensing of radiation/corrosion damages in protective coatings. Here, the surface/interface is coated with the layer under investigation. Changes in the optical properties and/or thickness of the probe layer as well as modification of the interface itself will affect the optical conditions at the interface and therefore the properties detected. The use of multiple internal reflection at the surface/interfaces will enhance the sensitivity to small changes and increase at the same time the active probing area.

Fabrication of Heteroepitaxial Chalcopyrite Compound Semiconductor

The fabrication of heteroepitaxial chalcopyrite compound semiconductor can be achieved by liquid phase epitaxy (LPE), vapor deposition, or organometallic vapor deposition (OMCVD) utilizing reduced pressures ($10^{-5}$ mbar–100 mbar) up to super atmospheric pressures (100 bar). The growth of such heterostructures has been demonstrated using dimethylzinc (DMZ), diluted germane (0.33%), phosphine (10%) and disilane (0.2%) in $H_2$ during open-tube OMCVD growth of $Zn(Ge_{1-x}Si_x)P_2$ heterostructures on (001) and (111) GaP and Si substrate at 580° C. growth temperature [9–15]. The characterization of these heterostructures by transmission electron microscopy (TEM) and secondary ion mass spectrometry showed sharp interfaces between the layers and high purity of the epilayers as compared to bulk $ZnGeP_2$ single crystals grown by directional solidification.

The cladding layers can be deposited by various techniques: Epitaxial layers of $Ga_{1-x}Al_xP$ can be deposited by chemical beam epitaxy (CBE), organometallic vapor deposition (OMCVD, also called metalorganic vapor phase epitaxy, MOVPE), or molecular beam epitaxy (MBE). For deposition of $SiO_2$ or $Si_3N_4$ cladding layers, deposition techniques such as chemical vapor deposition (CVD), remote-plasma CVD, thermal oxidation processes, or electro-chemical deposition are described in the literature. $CaF_2$ can be evaporated, sputtered (electron beam, ion beam, etc.), or plasma-assisted deposited. $ZnS_{1-x}Se_x$ layers can be evaporated, sputtered or deposited via OMCVD.

As already mentioned above, for the integration of light source and detectors a variety of fabrication techniques may be used:

Hybrid-bonded structures that connect light source and detectors with the active element can be made with existing technology. For example, interconnected optical wave guides with integrated signal preamplifier or even more complex phase sensitive amplification circuits on the Si-substrate are already commercially available;

Monolithic integration of light source and detectors.

For a possible reuse of light source and detection electronic, exchangeable active sensor modules can be manufactured, which are coupled via optical interconnects and electrical components. Interconnected optical wave guides with integrated signal preamplifier or even more complex phase sensitive amplification circuits on the Si-substrate are already commercially available.

Signal Processing and Bayesian Parameter Estimation Method

Real systems and real materials often do not approximate the ideal conditions assumed in model developments. The detection of a particular molecular species and its concentration will be critically dependent on the data acquisition and the signal processing methodology for accurate discrimination. A general approach to the signal processing/discrimination has been developed. This approach is based on a conditional probabilistic reduction method known as Bayes' Rule. The uniqueness of employing the Bayesian method lies in the fact that very precise physical models can be built directly into the method. For example, atomic form factors, which characterize the electronic structure of various target molecules, can be used for cellular image enhancement. Or, "structure factors" (analogues to those used in x-ray diffraction), which characterize the signature of various concentrations of target molecules in solution. And, models which assess the influence of imperfections as material defects (native point defects, surface decomposition, etc.), non-ideal interface sharpness, and composition and thickness variations which may skew the signal information. The physical models can be determined from first principles if an adequate physical model of the system is already had, or phenomenologically from the system at hand. Indeed, it may also be determined by a complementary pairing of theoretical and empirical results.

As a starting point, it is assumed that measurements result in a set of data that is represented by a column vector D of dimension 1×N. If the data is multi-dimensionial it is assumed that the pixels, or voxels, can be ordered in such a way as to produce the data vector D, i.e., $D(d_1, d_2, \ldots, d_N)$. The data D can be modeled by a vector function, f, and n a noise component:

$$D = f(\alpha) + n, \quad \text{(Equation 1)}$$

$\alpha$ includes all the physical information, parameters, which arise in constructing a model to represent the data. n represents the system noise which in general is assumed to be additive and as with the physical model function, the noise can be represented empirically, theoretically (Gaussian, for example), or as a combination of both.

Because of the presence of noise, the inversion of Equation 1 is non-unique and statistical procedures are necessary to obtain information about $\underline{\alpha}$. To this end the following probability densities are defined:

$P(\underline{\alpha}|DI)$=Probability Density(confidence) that $\alpha$ is true, conditioned on $D$ and any other prior information $I$. (Equation 2a)

$P(D|\alpha I)$=Likelihood Function—Probability Density for the data $D$ to have information concerning $\underline{\alpha}$. (Equation 2b)

$P(\alpha|I)$=Prior Probability Density on $\alpha$. (Equation 2c)

$P(D|I)$=Probability Density for $D$. (Equation 2d)

Note that, $0 < P(\alpha|DI) < 1,$ (Equation 3a)

$P(\alpha|DI) = 1$ implies 100% confidence in $\alpha$ (Equation 3b)

$P(\alpha|DI) = 0$ implies $\alpha$ is ruled out (Equation 3c)

An estimation of $P(\alpha|DI)$, also known as the "sampling distribution," is obtained by using Bayes theorem:

$P(\alpha DI) = [P(D|\alpha I) P(\alpha|I)]/P(D|I)$ (Equation 4)

For the case of Gaussian white noise the sampling distribution can be written as $P(D|\alpha I) = \eta \exp(-[D-f(\alpha)]^\dagger \Sigma^{-2}[D-f(\alpha)]),$ (Equation 5)

where $\eta$ is a normalization constant and $\Sigma$ is the error covariant matrix for $\alpha$.

Two methods that have proven fairly successful and that are widely used in the estimation of $\alpha$ are the Maximum Likelihood (ML) method and the Maximum A Posteriori A (MAP) method. Both approaches are special cases of the Bayesian statistical method, as will be shown below.

The Maximum Likelihood (ML) Method corresponds to the case when no prior information is available for the estimation of $\underline{\alpha}$. Then, the parameter vector a: is estimated using $$\nabla_\alpha P(D|\alpha I) = 0. \quad \text{(Equation 6)}$$

For Gaussian noise this becomes $$\nabla_\alpha [D-f(\alpha)]^\dagger \Sigma^{-2}[D-f(\alpha)] = 0. \quad \text{(Equation 7)}$$

That is Eq. (7) corresponds to the minimization of the nonlinear least-squares error. Thus one can use standard least-squares optimization procedures to estimate $\alpha$.

In the Maximum A Posteriori (MAP) Method it is assumed that a prior estimate for $\alpha$, $\alpha_o$, is available and that the prior probability density is of Gaussian form.

For the special case when both the likelihood and the prior estimate are Gaussian, $\alpha$ can be estimated from the following set of equations:

$$P(\alpha|DI) = N \exp[-(\alpha-\alpha_o)^\dagger \sigma_\alpha^{-2}(\alpha-\alpha_o)], \quad \text{(Equation 8)}$$

and $$\chi = [D-f(\alpha)]^\dagger \Sigma^{-2}[D-f(\alpha)] + (\alpha-\alpha_o)^\dagger \sigma_\alpha^{-2}(\alpha-\alpha_o) \quad \text{(Equation 9)}$$

$$\nabla \alpha \chi = 0, \quad \text{(Equation 10)}$$

where N is a normalization constant and $\sigma_\alpha = \delta_{ij} \Sigma$, i.e., only the diagonal elements of $\Sigma$.

When the noise is taken as Gaussian the MAP method is equivalent to the minimization of $\chi$. Equation (10) results in an estimate of $\alpha$ clustered about $\alpha_o$. The clustering, or difference, will depend on just how close to the true value(s) $\alpha_o$ was to begin with. (For the special case of Gaussian noise the MAP method turns out to be equivalent to Ridge Regession.

Alternatively, an estimate of a: can be obtained by calculating its first moment:

$$<\alpha> = \int \alpha P(\alpha|DI) d\alpha. \quad \text{(Equation 11)}$$

The second moment, $$<\alpha\alpha> = \alpha\alpha P(\alpha|DI) \, d\alpha, \quad \text{(Equation 12)}$$

gives the variance(s) on the estimate of $\alpha$.

The physical model function f containing a set of parameters, such as the concentration of the target molecules, frequencies, decay rates, chirp rates (or any other quantities, which may be encountered in the measurement process) can be expanded in a set of basis functions $G_j$:

$$f(\alpha) = \Sigma B_j G_j(\alpha), \quad \text{(Equation 13)}$$

where the $B_j$ are the associated expansion coefficients. Appropriately constructed wavelets obtain directly from the measured data is an example of the basis functions that may be employed.

In view of the foregoing description, numerous modifications and alternative embodiments of the invention will be apparent to those skilled in the art. Accordingly, this description is to be construed as illustrative only and is for the purpose of teaching those skilled in the art the best mode of carrying out the invention. Details of the structure may be varied substantially without departing from the spirit of the invention, and the exclusive use of all modifications, which come within the scope of the appended claim, is reserved.

What is claimed:

1. An optical quantitative detection device comprising:
a nonlinear birefringent waveguide sensor having a top cladding layer with a top surface for interacting with a target molecule;
a second waveguide;
a second cladding layer optically coupling the nonlinear birefringent waveguide sensor to the second waveguide, wherein optical excitation of the sensor and optical excitation of the second waveguide enables quantitative discrimination of a target molecule.

2. The device as recited in claim 1 wherein the quantitative discrimination of the target molecule is by discrimination of energies associated with the target molecule.

3. The device as recited in claim 1 wherein the nonlinear birefringent waveguide sensor further comprises a chalcopyrite based heterostructure.

4. The device as recited in claim 1 wherein the second waveguide is a linear waveguide.

5. The device as recited in claim 1 wherein optical excitation of the nonlinear birefringent waveguide sensor and optical excitation of the second waveguide is enabled by a laser.

6. The device as recited in claim 5 wherein the frequency of optical excitation of the nonlinear birefringent waveguide sensor is tunable.

7. The device as recited in claim 6 wherein optical excitation is tunable by varying a launch angle of the laser and by change of refractive indices.

8. The device as recited in claim 1 wherein the quantitative discrimination is estimated using Bayes theorem.

9. The device as recited in claim 1 wherein the quantitative discrimination corresponds to surface induced phase changes.

10. The device as recited in claim 1 further comprising a third waveguide and a third cladding layer optically coupling the second waveguide to the third waveguide, wherein the third waveguide is optically excited.

11. The device as recited in claim 1 wherein the top surface of the top cladding layer is a thin sensitized surface reaction layer, the optical dielectric properties of the reation layer are altered upon reaction with a specific target molecule.

12. The device as recited in claim 1 wherein the second waveguide is comprised of a III–V compound.

13. The device as recited in claim 1 wherein the nonlinear birefringent waveguide sensor further comprises a strained II–V semiconductor multi-hetrostructure which acts as a nonlinear birefringent waveguide.

14. A multi-area sensor module comprising:
a plurality of sensor elements;
each sensor element sensitized for a particular molecular structure;
an optical waveguide optically coupled to the plurality of sensor elements enabling optical excitation of the plurality of sensor elements; and
a plurality of detectors wherein each one of the plurality of detectors is optically coupled to a corresponding one of the plurality of sensor elements;
wherein optical excitation of the plurality of sensor elements enables discrimination of a target molecule.

15. The device as recited in claim 14 wherein each sensor element comprises a nonlinear birefringent waveguide.

16. The device as recited in claim 15 wherein the nonlinear birefringent waveguide further comprises a chalcopyrite based heterostructure.

17. The device as recited in claim 15 wherein the nonlinear birefringent waveguide is coupled to a linear phase-frequency converter structure with integrated modulator.

18. The device as recited in claim 14 wherein optical excitation is enabled by a laser.

19. The device as recited in claim 18 wherein the frequency of optical excitation of the nonlinear birefringent waveguide sensor is tunable by varying a launch angle of the laser and by change of refractive indices.

20. The device as recited in claim 14 wherein the discrimination of a target molecule is estimated using Bayes theorem.

* * * * *